United States Patent [19]

Winters

[11] Patent Number: 5,059,176

[45] Date of Patent: Oct. 22, 1991

[54] VASCULAR SYSTEM STEERABLE GUIDEWIRE WITH INFLATABLE BALLOON

[76] Inventor: R. Edward Winters, One Launching Rd., Andover, Mass. 01810

[21] Appl. No.: 454,411

[22] Filed: Dec. 21, 1989

[51] Int. Cl.⁵ ............................................. A61M 25/10
[52] U.S. Cl. ....................................... 604/96; 606/194
[58] Field of Search .................................. 604/95–101; 128/657, 772; 606/191, 194, 192

[56] References Cited

U.S. PATENT DOCUMENTS

| | | | |
|---|---|---|---|
| 3,452,740 | 7/1969 | Muller | 128/772 |
| 3,452,742 | 7/1969 | Muller | 128/772 |
| 3,528,406 | 9/1970 | Jeckel et al. | 128/772 |
| 3,625,200 | 12/1971 | Muller | 128/772 |
| 3,631,848 | 1/1972 | Muller | 604/95 |
| 3,789,841 | 2/1974 | Antoshkiw | 128/657 |
| 3,833,003 | 9/1974 | Tarico | 606/192 |
| 4,545,390 | 10/1985 | Leary | 128/657 |
| 4,573,470 | 3/1986 | Samson et al. | 606/194 |
| 4,650,467 | 3/1987 | Bonello et al. | 604/95 |
| 4,793,350 | 12/1988 | Mar et al. | 604/96 |
| 4,811,743 | 3/1989 | Stevens | 128/772 |
| 4,838,268 | 6/1989 | Keith et al. | 604/96 |
| 4,848,344 | 7/1989 | Sos et al. | 606/194 |
| 4,873,983 | 10/1989 | Winters | 128/657 |
| 4,875,481 | 10/1989 | Higgins | 604/96 |
| 4,892,519 | 1/1990 | Songer et al. | 606/194 |
| 4,906,241 | 3/1990 | Noddin et al. | 604/96 |
| 4,917,088 | 4/1990 | Crittenden | 606/194 |
| 4,946,466 | 8/1990 | Pinchuk et al. | 604/96 |

*Primary Examiner*—C. Fred Rosenbaum
*Assistant Examiner*—William W. Lewis
*Attorney, Agent, or Firm*—John M. Brandt

[57] ABSTRACT

A dilatation steerable guidewire for use in the vascular system having an inflatable balloon at the distal end and a bi-directional fluid pressure actuated ball valve forward of the balloon position. The guidewire construction provides torque and direction for manipulating the guidewire through the anatomy while the valve regulates fluid emission from the tip of the guidewire for visualization or into the balloon for inflation and deflation and is originated by fluid pressure.

6 Claims, 1 Drawing Sheet

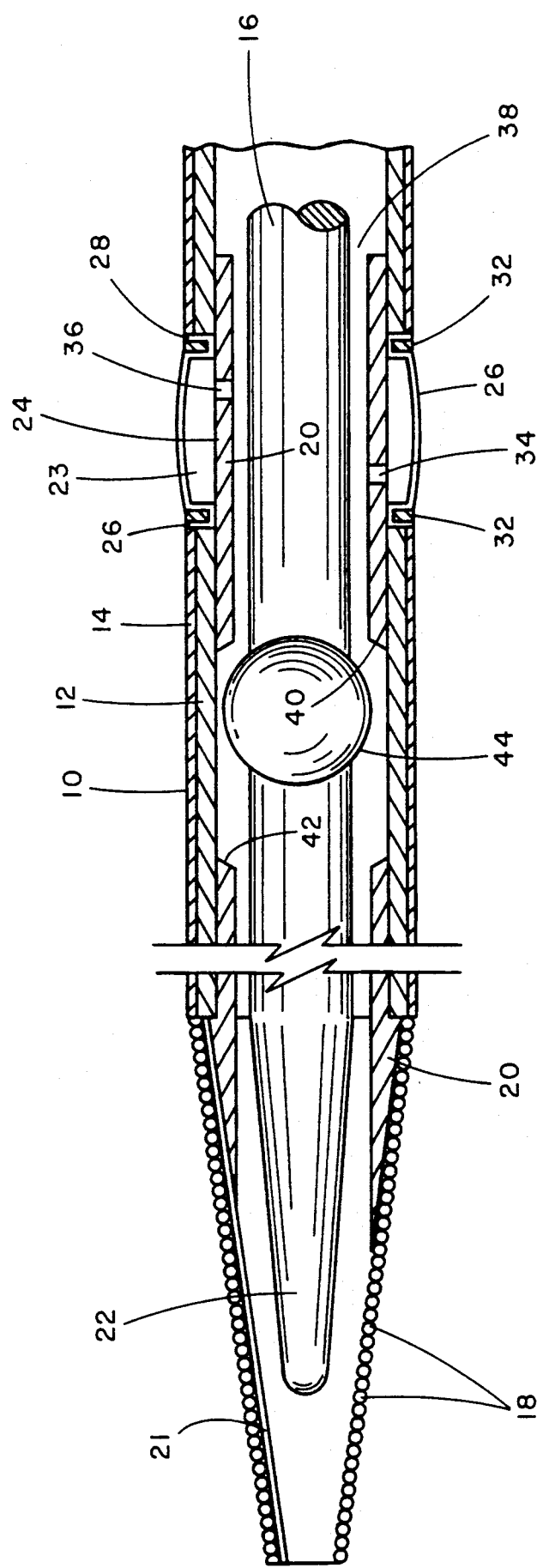

VASCULAR SYSTEM STEERABLE GUIDEWIRE WITH INFLATABLE BALLOON

BACKGROUND OF THE INVENTION

1. Field of the Invention

The invention resides in the field of guidewires for the insertion of catheters and other devices for the diagnosis and treatment of vascular disease.

Guidewires are small diameter devices which provide torsional, axial and radial rigidity and are utilized to insert catheters into the anatomy and to guide catheters into areas of vascular anatomy. Guidewires are generally constructed of materials such as stainless steel rod or tube stock and have a coiled metallic spring around their entirety or only at the distal end. The guidewire body, be it tube or rod, imparts torque and axial strength while the spring is soft to be atraumatic to the vascular tissue. Guidewires can vary in size of outer diameter from a few thousandths to 0.080 inches and are designated by diameter in thousandths of an inch. Steerable guidewires generally range in size of outer diameter from 0.010 inches to 0.020 inches.

Catheters are larger than guidewires and may be single or multiple lumen tubes of somewhat different construction and materials. They are designated by French size and vary from a few French to as large as 50 French for bypass surgery. One French equals 0.013 inches. Standard diagnostic catheters are generally made of a soft material such as plastic and are used for a variety of diagnostic and therapeutic applications. Diagnostic catheters are sometimes wire braid reinforced or of coaxial construction with the inner tube having more rigidity than the outer tube to provide some control to the catheter.

Steerable PTCA catheters vary from as small as 3 French to as large as 5 French. The smallest steerable catheter would be approximately 0.041 inches. Steerable catheters, unlike diagnostic catheters, do not generally have any reinforce-ment to provide torque characteristics. As such steerable catheters are guided into the vasculature and to the area of interest in the vasculature over steerable guidewires which provide torque and rigidity.

2. Description of the Prior Art

Prior to therapeutic catheters for the treatment of vascular disease, guidewires were used to straighten and safely guide diagnostic catheters into parts of the vascular system where radiopaque dyes were injected to illuminate the vasculature under fluoroscopy for studying the anatomy prior to therapy. With the advent of balloon and laser catheters for unblocking obstructions in small diameter vessels, such as the coronary arteries, came the development of highly steerable guidewires of small diameter for accessing these lesions. The necessity for highly steerable guidewire devices came as a result of the tortuous pathways encountered in the coronary vasculature. These steerable guidewires additionally were designed with very soft atraumatic tips to avoid injury to the vasculature. Typically for a balloon dilatation procedure, a small diameter steerable guidewire is placed within a small diameter multiple lumen balloon catheter and the two advanced into the vasculature through a larger diameter guide catheter which has been placed from a remote vascular entry point. The guide catheter is similar to diagnostic angiographic catheters and is placed over a large diameter guidewire which straightens the guide catheter for entry into a remote area of the vasculature and facilitates manipulation of the catheter. At this point the large diameter guidewire is removed and the preformed tip of the guide catheter enables the catheter which has some torque capability to be positioned at the site of entry of the therapeutic catheter into the particular area of the vasculature. The guide catheter, unlike a diagnostic catheter, is stiffer and designed with the added support capability to facilitate advancement of the steerable guidewire and balloon catheter assembly into the remote narrow vasculature. The guide catheter for coronary dilatation procedures would be advanced to the coronary ostium. From this point the dilatation catheter and steerable guidewire assembly, which have been advanced through the guide catheter as an assembly, would exit from the guide catheter into the coronary vasculature. The steerable guidewire would be advanced several centimeters out the tip of the balloon catheter. Because of the atraumatic tip and torque characteristics the steerable guidewire would be used to access the area of obstruction. The balloon catheter would then be advanced over the steerable guidewire across the lesion. The balloon on the catheter would then be inflated to accomplish the therapy. However, the steerable guidewire therefore would merely support the balloon catheter in reaching and crossing the lesion. With many steerable systems pressure could be measured from the tip of the balloon catheter in conjunction with a pressure from the guide catheter to provide a gradient. The amount of gradient pre and post dilatation could be used as a measure of success. With these steerable systems, the therapeutic catheter could then be pulled back on the steerable guidewire out of the narrowing to study the results by dye injection. The steerable guidewire remains across the lesion in order to re-cross the lesion if necessary for additional therapy or should there be closure of the vessel in order to re-open the vessel. Alternatively, the therapeutic catheter can remain across the lesion and the steerable guidewire removed to be exchanged for another steerable guidewire of varying characteristics should this be deemed necessary.

The use of these systems is well known and a variety of systems comprising various steerable guidewires and various balloon catheters in combination has been developed. The variety of steerable guidewires and catheters for facilitating the procedure is extensive.

For example, in the area of guidewires, U.S. Pat. Nos. 4,545,390, Leary, and 3,789,841, Antoshkiw, both show distal tips formed of helically wound springs surrounding fixed tapered cores. U.S. Pat. No. 3,631,848, Muller, describes an axially movable distal tip extension tube of relatively short length.

A coil tip with tapered face edges which will curve toward the taper when pulled upon by an internal control wire is disclosed in U.S. Pat. Nos. 3,452,740, and 3,452,742, both to Muller. U.S. Pat. No. 4,650,467, Bonello shows a similar arrangement for inclining the tip by retraction of a control wire affixed thereto.

Additionally, U.S. Pat. No. 3,528,406, Jeckel et al. teaches the use of a fixed core wire having a reduced diameter in the spring tip portion of the wire. U.S. Pat. No. 3,625,200, Muller, discloses a curvable tip comprising solid cylindrical links engaging each other with ball and socket joints each of which is manipulatable by a fine core wire. Finally, U.S. Pat. No. 4,573,470, Samson shows a curved tip which is rotated in its entirety by rotating a core wire at the control handle.

The aforementioned guidewire designs and improvements were limited to providing additional control characteristics to steerable guidewires to facilitate catheter placement.

In the area of balloon catheters for dilatation or compression of plaque, U.S. Pat. 4,323,071 discloses such a catheter in which two concentric tubes are employed, the inner tube adapted to fit over a separate steerable guidewire. The distal end of the outer tube is sealed to contain the fluid. Visualization of the anatomy by fluoroscopy may be accomplished ahead of the catheter and guidewire by infusion of dye through the central tube around the steerable guidewire and out the distal tip of the catheter.

An alternative system is described in U.S. Pat. No. 4,582,181, Samson et al. in which a balloon is similarly formed in a catheter outer tube having a separate guidewire extending therethrough and inflation fluid is delivered through a tube disposed side by side with the guidewire. In this system the guidewire is moveable within the catheter axially but the distal end is larger than the catheter tube through which it passes and as such may not be removed for guidewire exchange or may not be left in place while the catheter is removed for catheter exchange as is typical in standard steerable catheter and guidewire systems. Fluid may be infused in this system around the guidewire and out the distal tip of the catheter for dye tracing. The smaller wire permits a lower profile catheter system but obviates wire exchange.

Finally in U.S. Pat. No. 4,573,470, Samson et al. describes a Low-Profile Steerable Intraoperative Balloon Dilatation Catheter system wherein the catheter and the guidewire are bonded together to form a liquid-tight seal at the distal end of the catheter. The guidewire and balloon are manipulated as a unit with the guidewire fixed relative to the catheter to prohibit axial movement of the guidewire within the balloon catheter but enabling the guidewire to provide torque to the balloon catheter as an integral unit. In this system fluid is contained solely within the catheter.

The progression of developments in the area of steerable guidewire/catheter systems has enabled the access of smaller more tortuous vessels through the reduction of the overall outside diameter (profile) of the catheter/guidewire systems. In doing so the ability to provide distal dye injections, catheter exchanges and guidewire exchanges has been lost in some of these designs.

SUMMARY OF THE INVENTION

The present invention may be summarized as a vascular system dilatation steerable guidewire/balloon having an inflatable balloon disposed about the circumference of the distal end. The invention eliminates the usual catheter and guidewire combination entirely and incorporates the catheter features into the novel guidewire.

Fluid under appropriate pressure for inflating the balloon is introduced into the proximal end of the guidewire around a moveable but non-removeable core wire. Valves composed of valve seats formed from the guidewire walls distal to the balloon and a moveable ball valve member riding on a moveable core within the guidewire directs fluid into and out of the balloon through passageways in the guidewire walls under the balloon. Alternatively, the fluid is allowed to escape through the tip of the guidewire spring into the vascular system to carry out dye tracings in order to view the anatomy while guiding the device.

Additionally, a core member provides a means for controlling the distal coiled spring tip of the guidewire to dynamically change the guidewire characteristics in vivo. Thus, and as will be further seen from the disclosure below, the structure of the invention provides a multiplicity of features which have heretofore not been available in a steerable guidewire configuration.

The current invention provides desirable guidance/torque characteristics of steerable guidewires with the therapeutic capabilities of the balloon catheter while retaining the reduced overall profile of the guidewire device. In this manner there is no loss of steerability or therapeutic function. The design allows for distal dye injections, catheter exchanges and guidewire exchanges. In addition the design allows for increased control of the guidewiare dynamics through the ability to vary the stiffness of the guidewire tip in-vivo.

According to one embodiment of the present invention, the valve may be arranged to be sealed either by fluid pressure to provide forward motion of the ball valve member or backward motion by negative pressure through fluid withdrawal from the proximal end of the guidewire tube. Fluid pressure within the guidewire will accomplish forward valve closure and balloon inflation while fluid extraction from within the guidewire will accomplish closure of the rearwardly disposed seat by the ball valve member and will enable deflation of the balloon.

The stiffness of the coiled spring tip attached to the distal end of the guidewire tube is set by the choice of shape, coatings, materials, method of winding and diameters of the wire used to wind the coiled spring tip. The size, number and stiffness of the malleable safety wire(s) within the coiled spring tip determine the tip formability and contribute to the stiffness and torque of the coiled spring tip. Stiffness is also set by the shape and point of attachment of the inner distal connector tube within the coiled spring tip. The connector tube attaches the coiled spring tip to the body of the guidewire. The connector also provides the forward valve seat. Dynamic in-vivo control of tip stiffness is accomplished by advancement and retraction of the inner moveable core member with the attached distal stiffening member. The ball valve member rides on the moveable core member proximal to the distal stiffening member. The moveable core member forward motion, is controlled by advancing or retracting the proximal end of the moveable core member which exits from the proximal end of the guidewire tube. The inner moveable core member is of small diameter to allow fluid passage around the moveable core member from the proximal to distal end of the guidewire and, as such, does not provide additional frictional torque to the outer body of the guidewire, the guidwire thus functions as a standard steerable guidewire but with in-vivo variable tip stiffness.

To augment this capability, the balloon may be disposed in a recessed area of the guidewire wall such that the overall profile of the guidewire remains uniform; however this is not a requirement of the device wherein the balloon may be mounted on the exterior of the guidewire without a recessed area. This embodiment allows a conventional steerable balloon catheter to be placed over the guidewire as in a conventional steerable dilatation prodedure or for the exchange of a dilatation catheter or the exchange of the steerable guidewire/balloon invention for a conventional steerable guidewire during a procedure, thereby utilizing the device as a standard steerable guidewire.

The features and advantages of the invention will be more clearly understood from the description of the preferred embodiment and drawing which follow.

DESCRIPTION OF THE DRAWING

The Figure is a cross-sectional view of the preferred embodiment of the invention.

DESCRIPTION OF THE PREFERRED EMBODIMENT

Referring to the Figure a cross-sectional illustration of the steerable guidewire/balloon comprising the preferred embodiment of the invention is shown in which flexible tube 10 is composed of stainless steel (or other suitable guidewire material). Inner tube 12 may be coated with an outer lubricious surface 14 such as teflon. Within tube 10 is a moveable core 16. Helically wound spring tip 18 is attached to the distal end of tube 10 by connector 20. Tip 18 may be tapered as shown and is composed of stainless steel wire or other suitable radio dense material, such as platinum. Within spring tip 18 is safety wire 21 which is attached to the spring tip 18 and to connector 20 to prevent spring tip 18 from uncoiling. Stiffening member 22 is attached to, or an integral unit with core 16 and slidably fits within spring tip 18.

Recess 23 may be formed in tube 10 by, for example, cylindrical connector 24 and tube walls 26 and 28. Balloon 26 may be disposed in recess 23 and attached to connector 24 by any suitable adhesive. Metallic bands 32 may additionally be applied to further secure the balloon and provide bright radio opaque markers. Ports 34 and 36 in connector 24 communicate with space 38 formed between core 16 and wall 12 and allow fluid within space 38 to enter into or exit from recess 23 for balloon inflation and deflation.

Connector 24 has valve seat 40 formed on the end thereof forward of the position of the balloon. An additional valve seat 42 on connector 20 is positioned forward of seat 40.

Ball valve member 44 is slidably mounted on moveable core 16. When ball valve member 44 is in the appropriate contact position on either seat 40 or 42 it prevents fluid passage. Forward motion and seating of the ball valve member 44 is accomplished by fluid infusion and consequently fluid pressure within space 38. Rearward motion and seating of the ball valve member 44 is accomplished by fluid withdrawal and consequently negative fluid pressure within space 38.

As will now be seen the apparatus disclosed above functions in the previously described manner to direct fluid either into the balloon for inflation or if the valve seat is not engaged, as shown, past the valve and out the tip of tube 10 into spring tip 18 and out through the spring tip.

Further the ball valve will move to the rearward seat 42 when fluid is withdrawn from the proximal end of tube 10 to deflate the balloon.

It will also be seen that the steerable guidewire/balloon may operate independently of the fluid transfer function as a guidewire of varying tip stiffness by axial movement of the core member 16 and stiffening member 22 and consequently stiffening spring tip 18.

Additionally, when the balloon is optionally disposed in recess 23 as is shown, a catheter of larger diameter may be advanced over tube 10 in accordance with standard guidewire procedures and techniques as is practiced in the art. Likewise a suitable larger lumen balloon catheter may be advance over tube 10 when there is no recessed area.

Having fully described the configuration and method of use of the steerable guidewire/balloon comprising the invention, the scope of the patent is hereby defined by the following claims.

What is claimed is:

1. For use in the vascular system a steerable guidewire/balloon apparatus comprising in combination:
   a. a length of flexible tubing having proximal and distal ends and interior and exterior walls and providing torsional, axial and radial rigidity;
   b. an inflatable balloon disposed about the exterior circumference of said tubing at said distal end, said tubing having a passageway between said interior and exterior walls for admitting fluid to said balloon;
   c. a flexible axially moveable core member disposed within and along the length of said tubing; and
   d. valve means disposed within said tubing forward of said passageway comprising a valve seat attached to said tubing and a ball valve member slidably mounted on said moveable core for containing said fluid within said tubing and selectively directing said fluid into said passageway and said balloon by sealing said valve means by fluid pressure.

2. The apparatus of claim 1 wherein said valve seat is positioned to be sealed by said ball valve member by moving said member toward said distal end of said tubing by fluid pressure.

3. The apparatus of claim 1 wherein said valve seat is positioned to be sealed by said ball valve member by moving said member toward the proximal end of said tubing by fluid extraction.

4. The apparatus of claim 1 wherein said tubing has an exterior circumferential recess and said balloon is disposed in said recess.

5. The apparatus of claim 1 further including:
   a. a helically wound spring attached to said distal end of said tubing, said spring terminating in a smooth rounded tip; and
   b. a spring stiffening member attached to said core member adapted to fit within said spring upon moving said core toward said distal end of said spring.

6. The apparatus of claim 5 wherein said spring and said spring stiffening member are mutually tapered toward said distal end.

* * * * *